United States Patent [19]

Sigmund et al.

[11] Patent Number: 5,653,250

[45] Date of Patent: Aug. 5, 1997

[54] VAPOR-LIQUID EQUILIBRIUM AND INTERFACIAL TENSION MEASURING APPARATUS AND METHOD

[76] Inventors: Phillip Sigmund, 135 McPhillips Ave., Ganges, British Columiba, Canada, V0S 1E0; Zahidah Mohamed Zain, No. 34 Jalan 3/24G, Wangsa Melawati, 53300 Kuala Lumpur, Malaysia; Dawood Mohamed Anwar Raja, 46, Persiaran Syed Putra, 50460 Kuala Lumpur, Malaysia; Muhammad Ekrami Daud, 43, Jalan L4, Phase 6A, Taman Melawati, 53100 Kuala Lumpur, Malaysia

[21] Appl. No.: 508,995

[22] Filed: Jul. 28, 1995

[51] Int. Cl.[6] .................................................. G01N 7/00
[52] U.S. Cl. .............................. 137/7; 137/89; 137/154; 73/19.01
[58] Field of Search ........................ 137/7, 88, 89, 137/154; 73/19.01

[56] References Cited

U.S. PATENT DOCUMENTS

| 2,380,082 | 7/1945 | Sloan | 73/19.01 X |
|---|---|---|---|
| 3,276,460 | 10/1966 | Feld | 137/7 |
| 3,528,440 | 9/1970 | Plucker | 137/88 X |
| 3,731,530 | 5/1973 | Tanguy et al. | 73/19.01 X |
| 4,924,695 | 5/1990 | Kolpak | 73/61 |
| 4,970,891 | 11/1990 | Blevins et al. | 73/19.01 |
| 5,201,219 | 4/1993 | Bandurski et al. | 73/153 |
| 5,243,848 | 9/1993 | Cox et al. | 73/19.05 |

OTHER PUBLICATIONS

Copy of Ruska Instrument Corporation's Information and Specification Sheet Re Model 2370 PVT System Dated 1991.

*Primary Examiner*—Stephen M. Hepperle
*Attorney, Agent, or Firm*—Shlesinger, Arkwright & Garvey LLP

[57] ABSTRACT

An apparatus and method for facilitating the attainment of thermodynamic equilibrium and for measurement of interfacial tension of mixtures. A fixed volume chamber is connected at an upper end face and lower wall portion of the chamber to a first variable volume chamber and at a lower end face and upper wall portion of the chamber to a second variable volume chamber. Conduit valves and a valve controller control the flow of mixtures between the first and second variable volume chambers and the fixed volume chamber to selectively cause more dense component of the mixture to flow through less dense component of the mixture and less dense component of the mixture to flow through more dense component of the mixture, the flow through occurring within the fixed volume chamber.

19 Claims, 8 Drawing Sheets

VAPOR-LIQUID EQUILIBRIUM AND INTERFACIAL TENSION MEASURING APPARATUS AND METHOD

BACKGROUND OF THE INVENTION

1. Field of the Invention

The present invention relates to an apparatus and method for setting a desired thermodynamic state and for facilitating the attainment of thermodynamic equilibrium and measurement of interfacial tension and phase behaviour. The invention is most applicable when a phase separation occurs at the specific thermodynamic state between a mixture of components having different compositions and densities. In addition, this invention relates to an apparatus and method for determining engineering properties of the mixture to facilitate extraction and refining of relevant components of fluid mixtures. These engineering properties include interfacial tension between the phases, and volumetric behaviour during isothermal or constant composition expansion and differential liberation.

2. Description of the Prior Art

It is well known in the field of reservoir engineering and in the chemical engineering technology referred to as supercritical extraction, that extraction of oil/gas/water mixtures from a host reservoir depends on the physical properties of these phases and the interfacial tension between them, which vary from situation to situation. In order to improve efficiency in extracting oil, well-known tests have been developed to determine the various physical characteristics of the phases in a particular situation. One of the principal elements of interest is the interfacial tension between phases of differing density that occurs during extraction processes. One method of determining interfacial tension is by measuring the shape properties of drop of a dense phase suspended in a less dense phase (the gas). This is generally referred to as the "pendent drop" technique. An example of a device used to measure interfacial tension using the pendent drop method is the pendent drop interfacial tension cell sold by Temco, Inc. of Tulsa, Okla. Manipulation of interfacial tension between two or more phases during extraction can be achieved by changing pressure or composition of the phases allowing engineers to improve the rate of extractant recovery during the extraction process.

Another important parameter associated with the phase behaviour of oil and gas mixtures or oil/gas/water mixtures relates to the relative volumes of the more dense and less dense phases, taken at several pressure/volume/temperature points of the mixture.

Often experiments involve isothermal expansion of constant mass mixtures, sometimes referred to as "constant composition expansion" or "fluid compressibility," are carried out. The sample is initially a homogeneous single phase, the pressure of the sample being above its saturation pressure. Total volume of the system is increased, with a corresponding pressure decline until a lower pressure limit is reached, determined by a phase transition attained by determining a discontinuity in the compressibility or by the occurrence of minute droplets (bubble point) of the mixture.

A further experiment is the differential liberation measurement which requires stagewise separation of the gas portion of a mixture by segregating the oil and gas phases as volume is increased and pressure declines. At each step the total gas is removed and volume of the gas phase, liquid phase and total volume are determined. This procedure is important in estimating the total volume of oil and gas in the reservoir available for production.

All of the above tests and measurements require that the mixture be at, or close to, thermodynamic equilibrium in order to obtain reliable results. In addition, some tests require separation of the oil and the gas phases to obtain, for example, volume measurements (as with differential liberation).

In the past, samples had to be removed from the reservoir or process site to a sophisticated testing laboratory to perform these various measurements and tests. In petroleum reservoir engineering applications, thermodynamic equilibrium of the mixture was attained by inserting the oil/gas sample in a fixed volume cell containing liquid mercury. The cell would then be vigorously shaken and the mercury in the cell would physically aid the oil and gas mixture to attain thermodynamic equilibrium. Measurements and tests would then be undertaken on the oil and gas sample. However, mercury is a relatively toxic and dangerous substance to be handled, particularly in a non-laboratory setting. At the same time, to facilitate optimal extraction of oil and gas mixtures, it is important to have test results and measurements provided to them at the reservoir site quickly. The use of a cell containing the mercury is also an inappropriate method of attaining thermodynamic equilibrium in certain situations because of chemical reactions between the mercury and the sample.

Attempts have been made to develop a mercury-free apparatus which would enable rapid attainment of sample thermodynamic equilibrium. One such apparatus has been developed by Ruska Instrument Corporation of Houston, Tex. as Model 2370PVT System. In order to reduce the time needed to reach thermodynamic equilibrium, the sample mixture is mixed through the use of an internal mixing ring, which is magnetically coupled to an external mixing collar, which physically moves the mixing ring within the cell. Our apparatus offers mercury-free advantages while also making it possible to measure interfacial tension and other mixing features.

SUMMARY OF THE INVENTION

The present invention relates to an apparatus for setting a desired P-V-T thermodynamic state and for facilitating thermodynamic equilibrium of mixtures of liquids, vapours or combinations thereof, the mixture including differing molecular components, the apparatus including:

(a) a fixed volume chamber having an upper portion and a lower portion defined by transversely disposed upper and lower end phases connected by a wall;

(b) a first variable volume chamber for containing primarily more dense components or phases of the mixture;

(c) a second variable volume chamber for containing primarily less dense components or phases of the mixture;

(d) an upper end conduit having a first end extending through the upper end phase adjacent the upper portion into the fixed volume chamber and a second end connected to the first variable volume chamber;

(e) a lower end conduit having a first end extending through the lower end phase adjacent the lower portion into the fixed volume chamber and a second end connected to the second variable volume chamber;

(f) an upper wall conduit having a first end extending through the wall adjacent the upper portion into the fixed volume chamber and a second end connected to the second variable volume chamber;

(g) a lower wall conduit having a first end extending through the wall adjacent the lower portion into the fixed volume chamber and a second end connected to the first variable volume chamber;

(h) an upper end conduit valve connected to the end conduit for controlling the flow of mixture through the upper end conduit;

(i) a lower conduit valve connected to the lower end conduit for controlling the flow of the mixture through the lower end conduit;

(j) an upper wall conduit valve connected to the upper wall conduit for controlling the flow of the mixture of the upper wall conduit;

(k) a lower wall conduit valve connected to the lower wall conduit for controlling the flow of the mixture through the lower wall conduit;

(l) a valve controller for selectively controlling the positions of the upper end conduit, lower end conduit, upper wall conduit and lower wall conduit valves to orient the valves in open or closed positions to direct the flow of mixture between the first and second variable volume chamber and the fixed volume chamber to selectively cause more dense component of the mixture to flow through less dense component of the mixture and less dense component of the mixture to flow through more dense component of the mixture, the flow through occurring within the fixed volume chamber.

A method in accordance with the invention is also provided for attaining substantial thermodynamic equilibrium of mixtures of liquids, vapours or combinations thereof, the mixtures comprising components of different densities, in an apparatus having a fixed volume chamber connected to a first variable volume chamber containing primarily the more dense component and a second variable volume container containing primarily the less dense component, including the steps of:

(a) simultaneously introducing a flow of the more dense component from the first variable volume chamber into an upper region of the fixed volume chamber and exhausting less dense component into the second variable volume chamber from the upper region of the fixed volume chamber whereby the more dense component flows through the less dense component in the upper region of the fixed volume chamber;

(b) simultaneously introducing a flow of less dense component from the second variable volume chamber into a lower region of the fixed volume chamber and exhausting more dense component from the lower region of the fixed volume chamber whereby the less dense component flows through the more dense component in the lower region of the fixed volume chamber;

(c) monitoring the pressure in the fixed volume chamber;

(d) regulating the volume in the first and second variable volume chambers during steps (a), (b) and (c) to maintain a constant predetermined pressure in the fixed volume chamber and monitoring the pressure in the fixed volume chamber; and (e) repeating steps (a), (b), (c) and (d) until the change in volume of the first and second variable volume chambers require to maintain the constant predetermined pressures below a predetermined volume amount indicative of substantial thermodynamic equilibrium in the fixed volume chamber.

The method described above may further include the steps of:

(f) simultaneously introducing a flow of the less dense component into the lower region of the fixed volume chamber and exhausting more dense component from the lower region of the fixed volume chamber whereby the less dense component flows through the more dense component in a lower region of the fixed volume chamber;

(g) simultaneously introducing a flow of the more dense component into an upper region of the fixed volume chamber and exhausting less dense component from a lower region of the fixed volume chamber whereby the more dense component flows through the less dense component in the upper region of the fixed volume chamber;

(h) regulating the total volume in the first and second variable volume chambers during steps (f) and (g) to maintain the total volume in the first and second variable volume chambers substantially constant; and (i) repeating steps (f), (g) and (h) until a change in pressure in the fixed volume chamber is below a predetermined amount indicative of substantial thermodynamic equilibrium of the mixture in the fixed volume chamber.

DESCRIPTION OF THE PREFERRED EMBODIMENT

Figure 1:
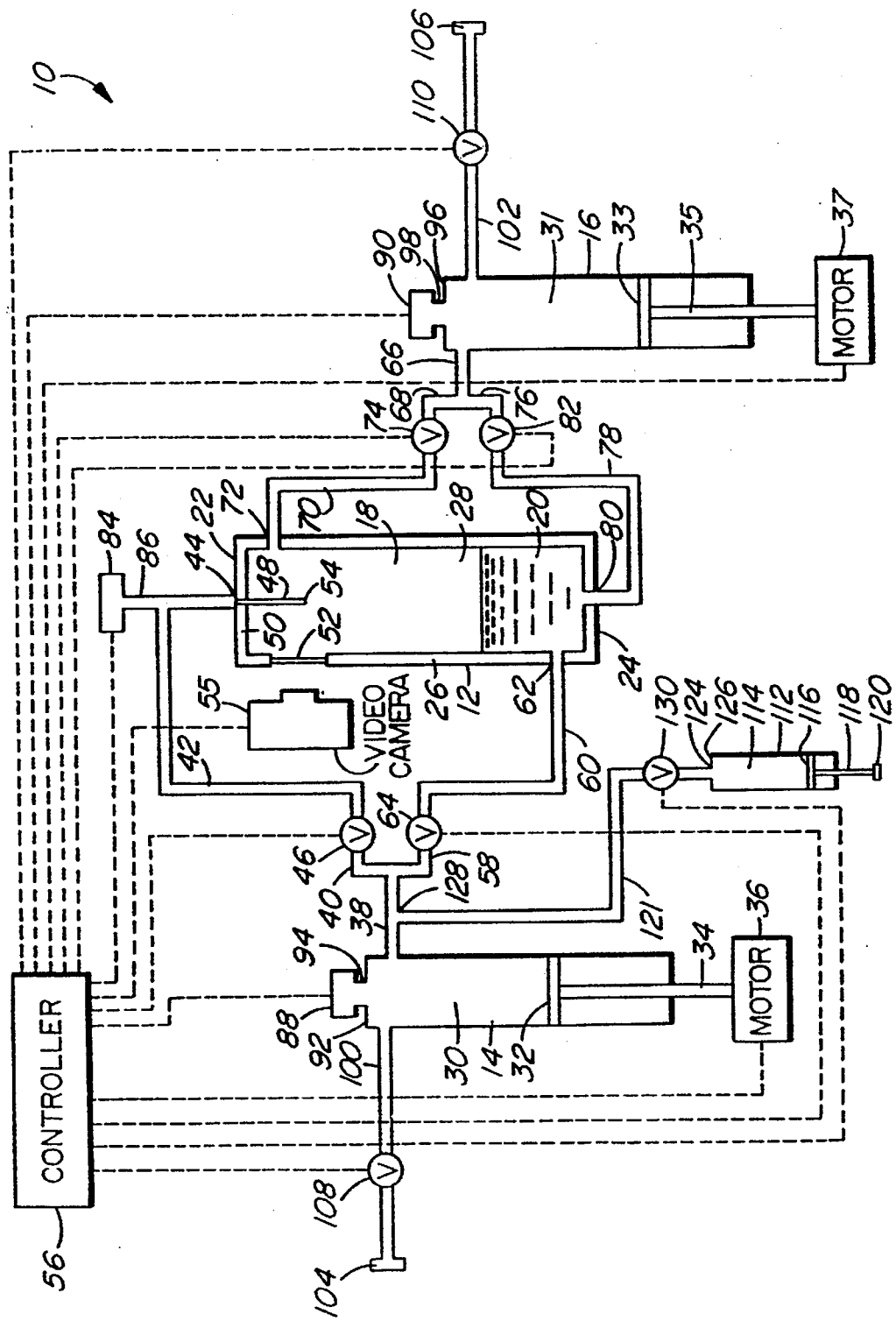
FIG. 1 is a schematic diagram of the apparatus of a preferred embodiment of the present invention.

Referring to FIG. 1, apparatus 10 for setting a desired thermodynamic state and for facilitating the attainment of thermodynamic equilibrium between a mixture of components having different molecular constituencies is shown schematically. Apparatus 10 includes a fixed volume chamber 12, first variable volume chamber 14, and second variable volume chamber 16. First variable volume chamber 14 is intended eventually to contain the equilibrated more dense phase of the mixture and a second variable volume chamber 16 is intended to contain primarily less dense phase of the mixture. Fixed volume chamber 12 is intended to contain two or more phases and is oriented with an upper portion 18 for primarily less dense phase of the mixture and lower portion 20 for containing primarily more dense component of the mixture, the upper portion 18 being above lower portion 20.

Fixed volume chamber 12 may be of cylindrical shape, constructed to withstand high pressure to 10,000 psi inside the chamber 12. Chamber 12 comprises a pair of transversely disposed upper and lower end faces, 22 and 24, respectively. Upper and lower faces 22 and 24 are circular in shape and are connected by cylindrical wall 26. Upper end face 22 defines the upper extent of upper portion 18 and lower end face 24 defines the lower extent of lower portion 20. Upper end face 22, lower end face 24 and wall 26 form opening 28 therebetween for containing and mixing components of the mixture. Chamber 12 is of fixed volume and faces 22 and 24 and wall 26 are integrally formed to retain their shape within the pressure limits provided above.

First and second variable volume chambers 14 and 16 are generally to be identical, although cylinders of differing volume and shape may optionally be employed. First chamber 14 includes cylindrical chamber 30 for housing a phase or component of the mixture. Second chamber 16 includes cylindrical chamber 31 for housing another phase or component of the mixture. The volume of chambers 14 and 16 may be varied by means of pistons 32 and 33 respectively disposed within respective chambers 30 and 31 for reciprocal upward and downward movement of pistons 32 and 33 to vary the volume above the piston, such volume being connected to chamber 12 in the manner hereafter described. As pistons 32 and 33 are moved upwardly, the respective volume above pistons 32 and 33 in chambers 30 and 31 decreases. Conversely, as pistons 32 and 33 are moved downwardly, the respective volume above pistons 32 and 33 in chambers 30 and 31 increases. Pistons 32 and 33 are connected to respective nuts on ball screws 34 and 35; the other ends of ball screws 34 and 35 being connected by worm gears to respective motors 36 and 37. Motors 36 and 37 cause respective ball screws 34 and 35 to rotate and hence nuts and eventually pistons 32 and 33 to reciprocate upwardly or downwardly within cylindrical chambers 30 and 31. As well, motors 36 and 37 contain calibrating means (not shown) for determining the position of piston rods 34 and 35 and pistons 32 and 33 in chambers 30 and 31 to permit accurate calculation of the volume of chambers 30 and 31 above respective pistons 32 and 33. Motors 36 and 37, incorporating the calibration feature, are well known in the art and include, for example, model DX100 manufactured by Isco.

First and second chambers 14 and 16 are connected to fixed volume chamber 12 by means of several conduits, as will be described, made of stainless steel and able to withstand pressures to 10,000. Referring initially to the connection of conduits between first variable volume chamber 14 and fixed volume chamber 12, first variable volume outlet conduit 38 extends laterally adjacent to the upper end of chamber 30 of the first variable volume chamber 14. Conduit 38 splits to form a second end 40 of upper end conduit 42; the first end 44 of upper conduit 42 is connected to upper end face 22 of chamber 12; upper end conduit valve 46 is connected to the upper end conduit to control the flow of mixture through the upper end conduit. When valve 46 is in a closed position, no mixture may flow through upper end conduit. When valve 46 is in the open position, mixture may flow between the chamber 30 of first variable volume chamber 14 and upper portion 18 of chamber 12.

First end 44 is connected to capillary tube 48 to control the flow of mixture from first end 44 through capillary tube 48 into upper portion 18. First end 44 extends longitudinally through the central axis of upper end face 22. Capillary tube 48 is of stainless steel construction having an inner diameter of about 0.08 millimeters and an outer diameter of about 1.5 millimeters and extends approximately 20 millimeters into upper portion 18 from inner face 50 of upper end face 22.

Fixed volume chamber includes window 52 which is clear and of suitable material and strength to withstand pressure in upper portion 18 equivalent to the strength of wall 26 and end faces 22 and 24. Window 52 is clear and permits video camera 55 to take video pictures of the upper portion 18, including mixture flowing out of end 54 of capillary tube 48.

Camera 55 may be a micro video camera including a frame grabber attachment and necessary software to provide image analysis of either a single drop or sequence of drops of mixture flowing out of end 54. These images are used to analyse drop shape and to estimate average drop volumes and provide that information to the operator or computer controller 56 as is described below.

Conduit 38 is split to connect with second end 58 of lower wall conduit 60. First end 62 of lower wall conduit extends through wall 26, laterally into lower portion 20 of fixed volume chamber 12. Lower wall conduit valve 64 is connected to the lower wall conduit to control the flow of mixture through the lower wall conduit. When valve 64 is in a closed position, no mixture may flow through lower wall conduit between outlet 38, connected, in turn, to chamber 30 and fixed volume chamber 12.

Second variable volume chamber 16 is similarly connected to fixed volume chamber 12. Second variable volume outlet conduit 66 extends laterally from an upper portion of chamber 31. Second end 68 of upper wall conduit 70 is connected to conduit 66; first end 72 of upper wall conduit 70 extends laterally through wall 26 adjacent inner face 50, into upper portion 18. Upper wall conduit valve 74 is connected to upper wall conduit 70 to control the flow of mixture through upper wall conduit 70. When valve 74 is in a closed position, no mixture may flow between conduit 66, which is connected to chamber 31 of second variable volume chamber 16 and fixed volume chamber 12, through upper wall conduit 70.

Second end 76 of lower end conduit 78 is also connected to the end of conduit 66 opposite to the end connected to chamber 31 of second variable volume chamber 16. First end 80 of conduit 78 is connected longitudinally along the axis of chamber 12 through the central axis of face 24. Lower end conduit valve 82 is connected to lower end conduit 78 for controlling the flow of mixture through lower end conduit 78. When valve 82 is in an open position, mixture may flow between conduit 66, connected to chamber 31 of second variable volume chamber 16 and fixed volume chamber 12 through end 80. When valve 82 is in its closed position, mixture cannot flow through conduit 78 between end 80 and end 76.

Fixed volume chamber 12 is connected to pressure transducer 84 to determine the pressure within opening 28. Pressure transducer 84 is connected to conduit 86, which, in turn, is connected to upper end conduit 42. It can be seen that pressure in opening 28 is the same as pressure in conduit 86, measured by pressure transducer 84. Transducer 84 enables measurement of pressure in opening 28 on a continuous basis during operation of apparatus 10.

Similarly, first and second variable volume chambers 14 and 16 have respective pressure transducers 88 and 90 connected to respective chambers 30 and 31 above pistons 32 and 33 to determine the pressure in chambers 30 and 31 on a continuous basis. Transducer 88 is connected to the upper end face 92 of chamber 30 by means of conduit 94. Similarly, pressure transducer 90 is connected to upper end face 96 of chamber 31 by means of conduit 98.

First and second variable volume chambers 14 and 16 include input conduits 100 and 102, respectively, extending laterally from respective chambers 30 and 31 adjacent respective upper end faces 92 and 96. Conduits 100 and 102 include respective sample input ports 104 and 106 which may be connected to the sample of mixture to be analyzed. Preferably, less dense phase or components of the sample mixture are input through sample port 106 and more dense phases or components of sample mixture are input into apparatus 10 through sample input port 104. Although this is not critical to application of the art. Input valve 108 is connected to conduit 100 to direct the flow of mixture between sample input port 104 and chamber 30 of first variable volume chamber 14. Valve 110 is connected to conduit 102 to divert the flow of mixture between sample input port 106 and chamber 31 of second variable volume chamber 16. When valve 108 is in an open position, mixture may flow between port 104 and chamber 30 of first variable volume chamber 14. When valve 108 is closed, mixture is prevented from flowing. When valve 110 is in an open position, mixture may flow through conduit 102 between port 106 and chamber 31 of second variable volume chamber 16. When valve 110 is closed, mixture is prevented from flowing through conduit 102.

As will be discussed later, it is important to carefully control the drop wise flow of mixture through end 54 of capillary tube 48 into opening 28. In practice it is advantageous to provide manual pressure volume control in conduit 42, to enable manual control of the drop wise flow of mixture out end 54, manual variable volume chamber 112 is provided. Chamber 112 includes cylinder 114 with piston 116 positioned therein for up and down reciprocal motion of piston 116 in cylinder 114; piston 116 is connected to shaft 118 which, in turn, is connected to handle 120 for manual actuated movement of piston 116 upwardly or downward in cylinder 114. The portion of cylinder 114 above piston 116 is connected to hand pump conduit 122. First end 124 of conduit 121 is connected axially to upper end face 126 of cylinder 114. Second end 128 of conduit 121 is connected to conduit 38. This enables pressure to be applied to conduit 38 and conduit 42 on movement of handle 120 upwardly to decrease the volume of cylinder 114 above piston 116. An operator can thereby control the drop wise flow of mixture through end 54 by manual application of pressure or decrease in pressure in conduit 121. Manual variable volume chamber valve 130 is connected to conduit 121 to control the flow of mixture through conduit 121 between chamber 112 and conduit 138.

Normally, the manipulation of the valves and pistons 32 and 33 of respective first and second variable volume chambers 14 and 16 may be controlled by controller 56 which is preferably a computer having multiple input means for receiving and sending electrical signals between controller 56 and specific valves or motors 36 and 37, as required. In addition, pressure transducers 84, 88 and 90 are connected to controller 56 to provide pressure data of the pressure inside chambers 12, 14 and 16. Controller 56 receives and sends signals to enable operation of apparatus 10 in the manner described under the heading OPERATION discussed below. As well, controller 56 may be used to send signals for the control of movement of mixture within apparatus 10 to perform various tests and experiments on the mixture in apparatus 10, including interfacial tension between the components, isothermal or constant composition expansion and differential liberation. The manipulation of the valves, and motors 36, based on signals from pressure regulators 84, 88 and 90, and camera 55, are discussed below as well. Electrical connection between controller 56 and the valves, regulators and camera are depicted in broken lines in FIGS. 1-4.

OPERATION

The operation of apparatus 10 will now be discussed with reference to FIGS. 2–5. FIGS. 2–5 provide a schematic representation at each step of the operation of apparatus 10, including the position of valves, pistons and mixture of components and phases for each of these steps. It should be understood that the operation steps relate to the preferred embodiment of this invention and are not intended to limit the more general aspects of this invention. Alternate flows and steps in moving the mixture of less dense component and more dense component through fixed volume chamber 12 will attain substantial thermodynamic equilibrium of the mixture. As well, while a part of the preferred embodiment, the alternate mixing of components, first at constant pressure of the mixture in apparatus 10, then at constant volume of the first and second variable volume chambers 14 and 16, is preferred, but is not intended to be limiting of the broader scope of this invention, as defined by the claims.

In order to provide accurate data from apparatus 10, samples of fluids from, for example, petroleum reservoir sites, must be obtained and introduced to the pumps at predetermined constant pressure and volume. The initial introduction of sample into apparatus 10 may be accomplished in several ways. Optionally, mixture from the sample container may be introduced by connection to sample input port 104 to a high-pressure seal between the sample container (not shown) and port 104. Valve 108 is then opened to permit the mixture to flow through conduit 100 into cylindrical chamber 30 of first variable volume chamber 14. Piston 32 may be positioned near the upper end of chamber 30 and moved downwardly toward the lower end of chamber 30 to cause the fluid to flow through conduit 100 into cylinder 30. Valve 108 may then be closed, valve 64 opened, and piston 32 moved upwardly to cause mixture to flow through conduit 60 into lower portion 20 of fixed volume chamber 12. The amount of mixture flowing into fixed volume chamber 12 may be controlled by the position of the piston during the opening or closing of valve 64.

Figure 2:
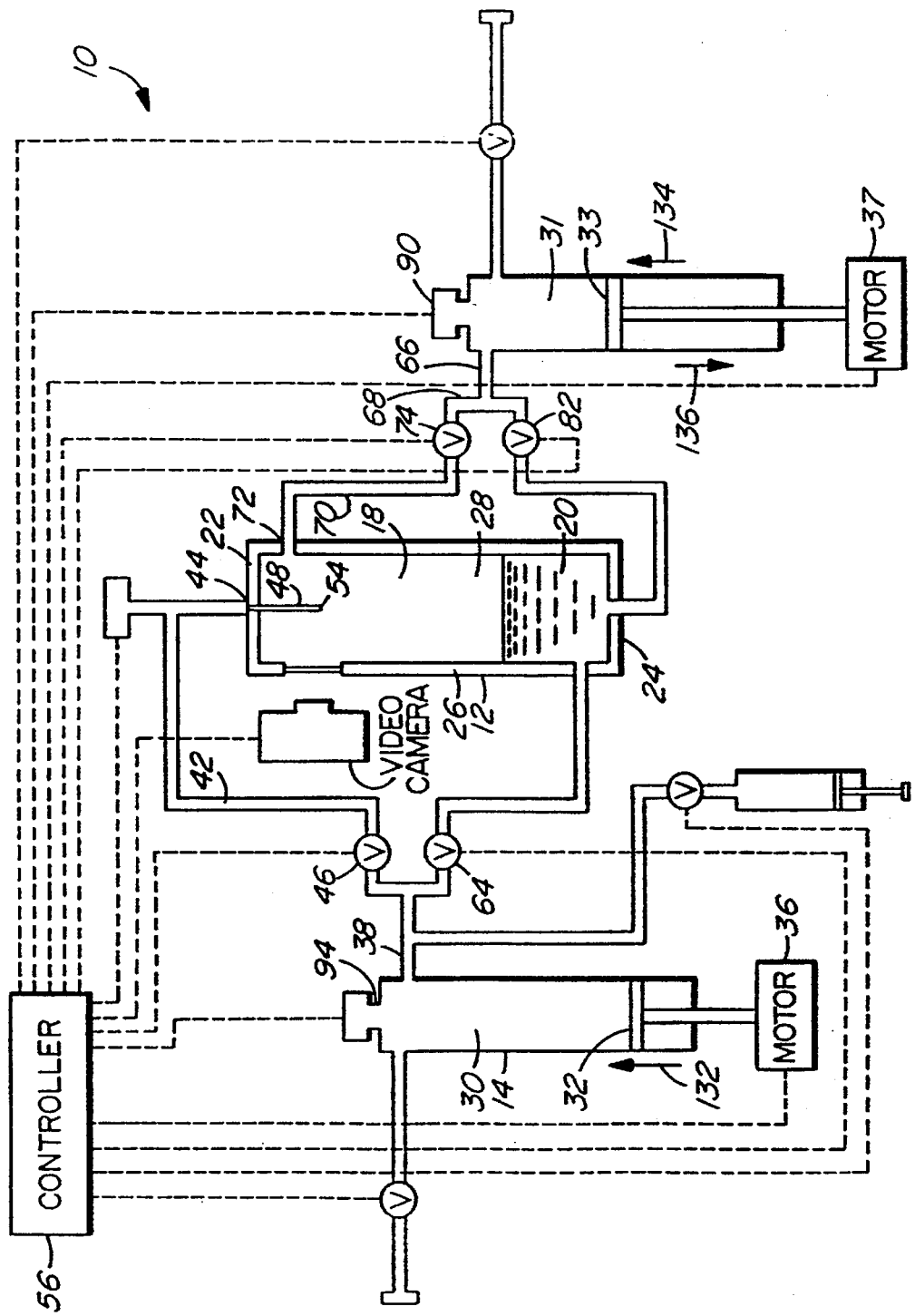
FIG. 2 is a schematic view of the apparatus of FIG. 1 depicting the initial circulation of components of the mixture at constant pressure.
Figure 3:
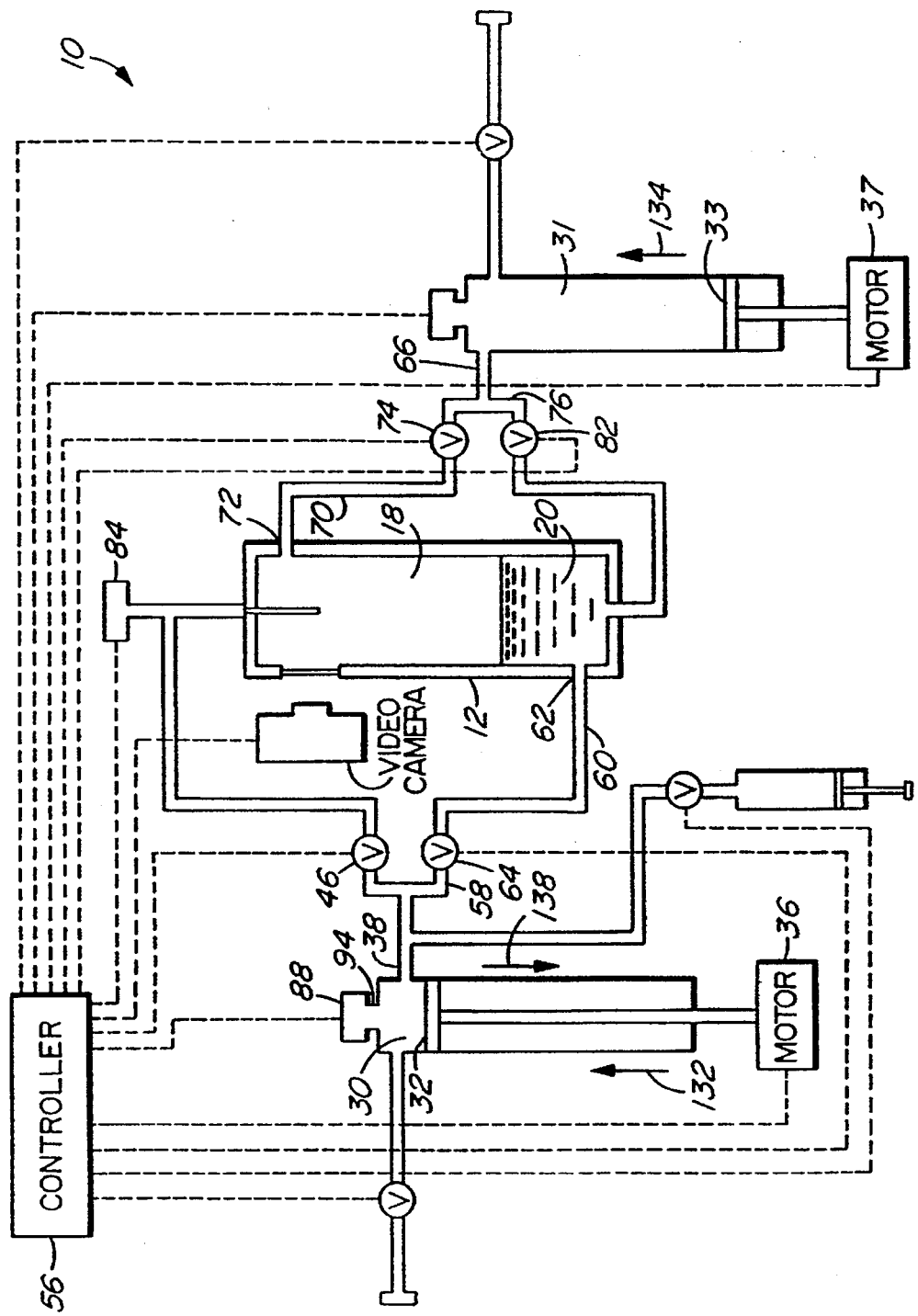
FIG. 3 is a schematic diagram of the apparatus of FIG. 1 depicting further circulation of components of the mixture at constant pressure.

After introducing samples in this way and mixing, the valves and pumps may be arranged so that fixed volume chamber 12 contains more dense components or phases in lower portion 20 and less dense components or phases in upper portion 18. At this point, the cycling of less dense and more dense components may commence. Referring initially to FIGS. 2 and 3, the initial circulation of components of the mixture occurs at constant pressure. The first step in the cycling process is depicted in FIG. 2. Controller 56 causes valve 46 and valve 74 to be positioned in the open position to permit flow of mixture through conduits 42 and 70, respectively. The other valves, including valves 64 and 82, remain in the closed position. Controller 56 activates motor 36 to cause piston 32 of first variable volume chamber 14 to move upwardly in the direction of arrow 132 to decrease the volume in chamber 30 above piston 32. At the same time, pressure transducer 90 determines the pressure in chambers 30 and 31 and in upper portion 18, which are now all connected due to the opening of valves 46 and 74. Pressure signals are sent to controller 56 from transducer 90. Controller 56 activates motor 36 to move piston 33 upwardly in the direction of arrow 134 or downwardly in the direction of arrow 136 to maintain substantially constant pressure in chambers 30 and 31 and in upper portion 18. As chamber 30 contains primarily more dense component, the more dense component is forced out of chamber 30 through conduits 38 and 42. The more dense component then passes through end conduit 44 into capillary tube 48 and then flows into upper portion 18 out of capillary tube end 54. Because of the dimensioning of capillary tube 48, a drop wise restricted flow may be selected whereby more dense component flows drop wise through the less dense component in upper portion 18 while mixing with it before commingling with the more dense phase lying in lower portion 20. This causes the level of more dense phase in lower portion 20 to rise as more and more dense component flows into chamber 12. This forces less dense component residing in upper portion 18 to be exhausted from upper portion 18 through first end 72 of conduit 70 and then through conduit 66 into chamber 31 above piston 33. This continues until substantially all of the more dense component in chamber 30 has been forced out of chamber 30 and piston 32 is in its upper position near the top end of chamber 30. Apparatus 10 then switches to perform step 2 of the cycling of the mixture under constant pressure, as depicted in FIG. 3.

Referring to FIG. 3, controller 56 signals valve 64 and valve 74 to cause the valves to move to their open position. Controller 56 also signals valve 46 to move to its closed position. All other valves remain in their closed positions. Controller 56 then signals motor 37 to cause piston 33 to move in an upward direction, in the direction of arrow 134, to force the primarily less dense component in chamber 31 out of chamber 31. Less dense component then flows through conduits 66 and 70, through first end conduit 72 into upper portion 18 of fixed volume chamber 12. This forces more dense component of the mixture in lower portion 20 out first end conduit 62 through conduits 58 and 38 into chamber 30. Pressure transducer 84 continuously monitors the pressure in upper portion 18 and provides pressure signals to controller 56. Controller 56, in turn, regulates the activation of motor 36 to move piston 32 upwardly, in the direction of arrow 132, or downwardly, in the direction of arrow 138, to maintain the pressure in at a substantially predetermined pressure level.

Steps 1 and 2, as described above with reference to FIGS. 2 and 3, are repeated and the change in pressure constantly monitored by transducers 84 and 90 until the change in pressure in apparatus 10, as the cycling steps are repeated, falls below a predetermined pressure change amount, indicative of substantial thermodynamic equilibrium of the mixture in apparatus 10. Controller 56 then changes to cycling of the mixture through apparatus 10 at constant volume, which will now be discussed with reference to FIGS. 4 and 5.

Figure 4:
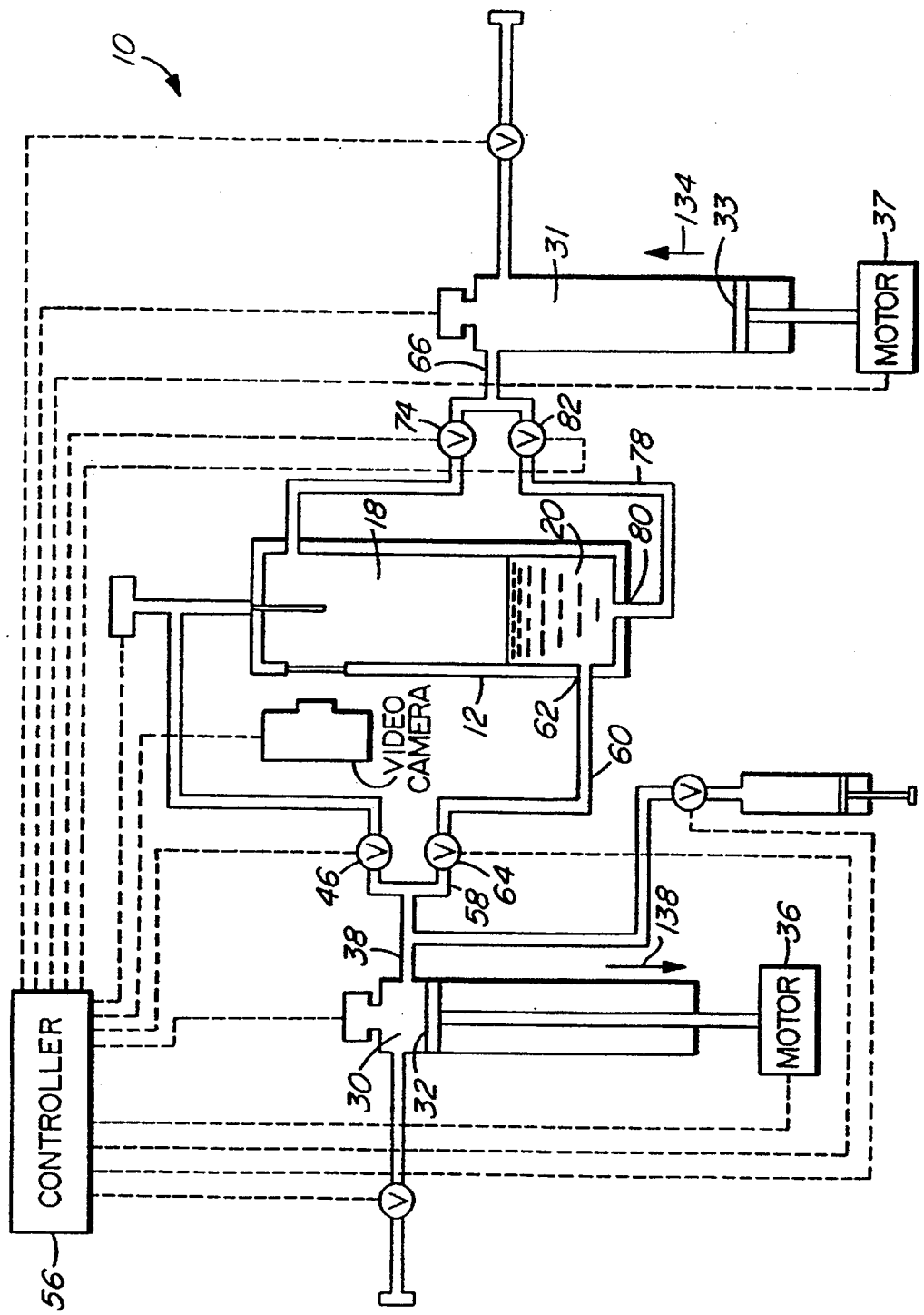
FIG. 4 is a schematic drawing of the apparatus of FIG. 1 depicting circulation of components of the mixture at constant volume.

Referring initially to FIG. 4, step 3 of the cycling process will now be discussed, with apparatus 10 set to control cycling of the mixture through apparatus 10 at substantially constant total volume between the areas above pistons 32 and 33. Controller 56 signals valve 74 to move to its closed position and valve 82 to move to its open position. Valve 64 remains in its open position and valve 46 remains in its closed position. All other valves remain closed. Controller 56 then signals motor 37 to move piston 33 from a position near the lower end of chamber 31 in an upward direction, in the direction of arrow 134, towards the top of chamber 31. This forces the primarily less dense component of the mixture in chamber 31 through conduits 66 and 78 into chamber 12 through first end 80. The less dense component bubbles through the more dense component in lower portion 20, mixing with it and segregating with the less dense component in upper portion 18. This forces more dense component in lower portion 20 out of chamber 12 through first end 62 into conduit 58. More dense component then moves through conduit 58 and conduit 38 into chamber 30. Controller 56 is continuously monitoring the change in volume above piston 33 based on the number of cycles of movement of motor 37. Controller 56 controls movement of piston 32 by controlling motor 36 so that, as the volume in chamber 31 above piston 33 decreases, volume above piston 32 in chamber 30 increases a corresponding amount to maintain the total volume in chambers 30 and 31, above pistons 32 and 33, respectively, at a constant predetermined volume amount. Consequently, as piston 33 is moved upwardly in the direction of arrow 134, piston 32 is moved downwardly in the direction of arrow 138. If the volumes in chambers 30 and 31 are substantially equal, as piston 33 is moved upwardly, piston 32 is moved downwardly an equal amount. Once piston 33 has moved upwardly to a position near the top of cylinder 31, substantially all of the less dense component in cylinder 31 has passed into upper portion 18. The cycling of mixture in apparatus 10 is then changed, which will be described with reference to FIG. 5.

Figure 5:
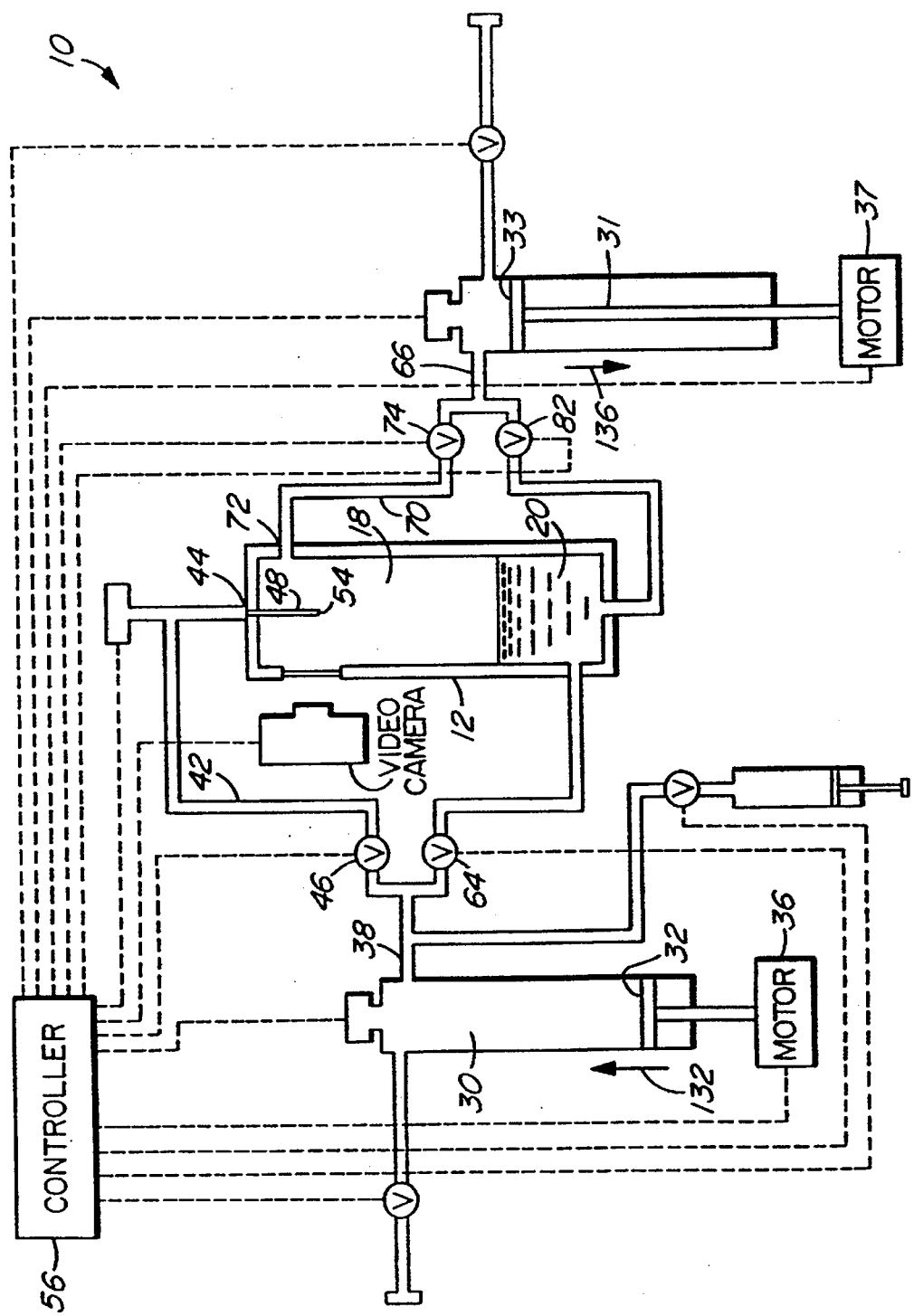
FIG. 5 is a further schematic diagram of the apparatus of FIG. 1 depicting circulation of components of the mixture at constant volume.

Referring to FIG. 5, controller 56 signals valve 64 to move to its close position and valve 46 to move to its open position. Controller 56 also signals valve 74 to move to its open position and valve 82 to move to its closed position. All other valves remain closed. Controller 56 then signals motor 36 to cause piston 32 to be moved in an upward direction in the direction of arrow 132. Motor 36 signals controller 56 data based on the movement of motor 36 to permit controller 56 to determine the decreasing volume in chamber 30 above piston 32. Controller 56 then actuates motor 37 to move piston 33 downwardly in the direction of arrow 136 a sufficient distance to maintain constant total volume in the area of chamber 30 above piston 32 and chamber 31 above piston 33. In this way, apparatus 10 is maintained at substantial constant total volume of area above pistons 32 and 33. This causes primarily more dense component in cylinder 30 to flow out of cylinder 30 into conduits 38 and 42. More dense component then flows through first end 44 and through capillary tube 48 to enter chamber 12 through end 54. Due to the dimensioning of capillary tube 48, more dense component exits end 54 in a drop wise flow through less dense component in upper portion 18. Controller 56 controls advancement of piston 32 in a manner which controls the amount of more dense component flowing through end 54 to obtain a drop wise flow of more dense component through less dense component in upper portion 18. More dense component flows into and mixes with more dense component in lower portion 20. This forces less dense component in upper portion 18 out of chamber 12 through first end 72 into conduit 70. Less dense component then flows through conduit 66 into chamber 31 above piston 33. This continues until piston 32 is moved substantially adjacent the upper portion of chamber 30 and piston 33 is moved downwardly substantially adjacent the lower portion of chamber 31. Step 3, as described above with reference to FIG. 4, and step 4, described herein with reference to FIG. 5, are then repeated with continuous monitoring of the movement of motors 36 and 37 to obtain continuous monitoring of the total volume in chambers 30 and 31 above pistons 32 and 33, respectively. When the change in total volume falls below a predetermined volume change amount, the cycling of mixture as described with reference to FIGS. 4 and 5 is terminated by controller 56. The change in total volume dropping below the set predetermined volume change level is indicative of thermodynamic equilibrium of the mixture having been attained in chambers 30, 31 and fixed volume chamber 12. Mixture phases in apparatus 10 are now ready for various testing to occur to determine various essential parameters of the phase mixture, such as interfacial tension, isothermal or constant composition expansion and differential liberation, which will be discussed with reference to FIGS. 6–8.

INTERFACIAL TENSION

Figure 6:
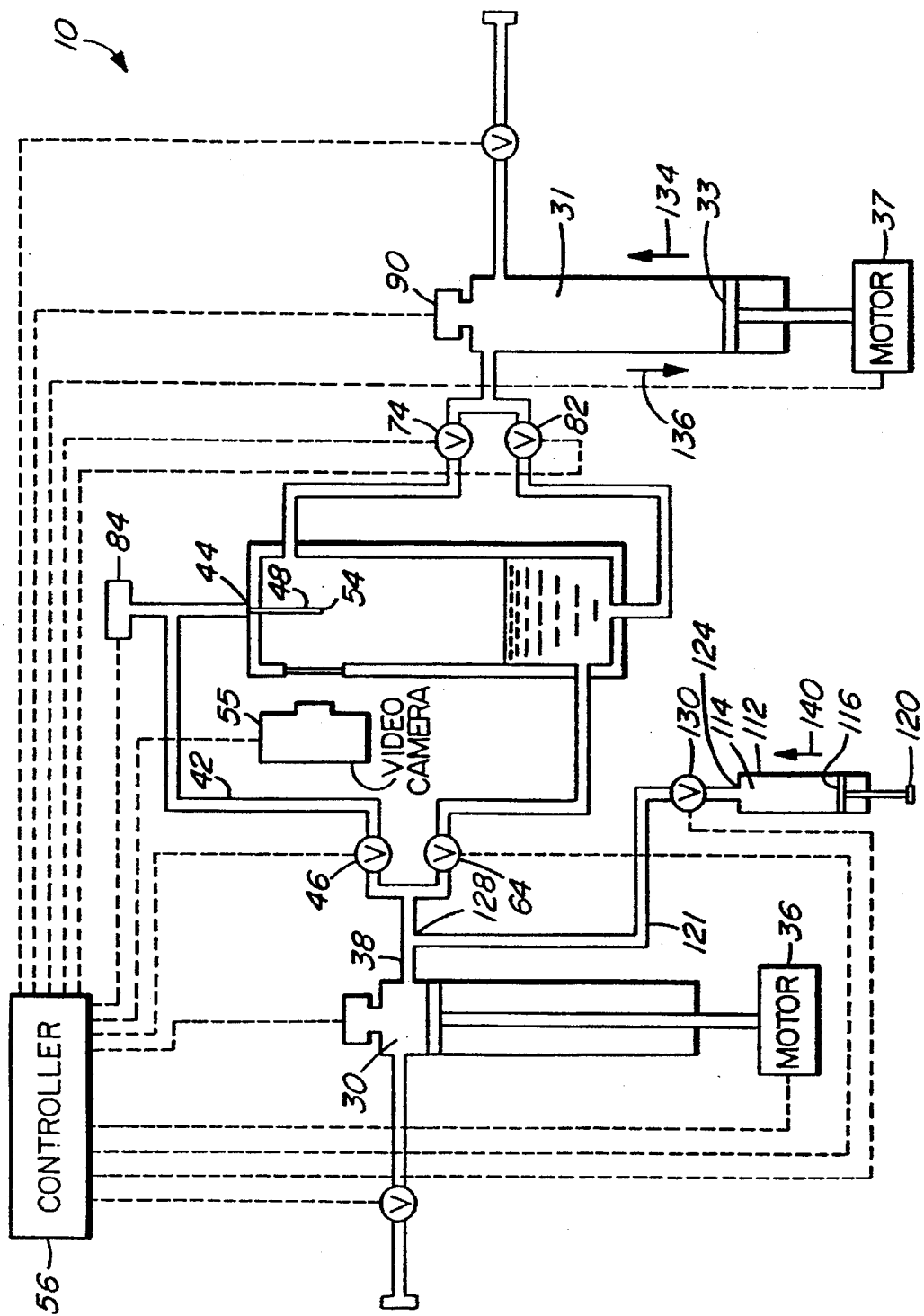
FIG. 6 is a schematic view of the apparatus of FIG. 1 depicting the use of the apparatus for the measurement of interfacial tension.

The use of apparatus 10 for the measurement of interfacial tension between the components of the mixture will be discussed with reference to FIG. 6. The pump is filled by placing controller 56 into constant pressure with respect to piston 32; this permits dense fluid to flow through conduit 38 while withdrawing piston 116 to a desired level.

Controller 56 signals valve 130 to move to its open position. Valves 46 and 74 remain in their open position and valves 64 and 82 remain in their closed position. The operator then manually moves piston 116, by means of handle 120, inwardly in the direction of arrow 140. This forces more dense component in cylinder 114 through conduit 121, exiting second end 128 into conduit 38. More dense component then flows through conduit 42 out first end 44 into capillary tube 48 and out end 54. The operator can then manually control the drop wise flow out end 54 to cause a drop to hang suspended from end 54. Controller 56 signals motor 36 to maintain piston 32 in a constant position so that no less dense component flows in or out of cylinder 30. Video camera 55, including frame grabber circuitry (not shown), takes video pictures of the drop suspended from end 54 and passes signals corresponding to the physical characteristics of the drop to controller 56. Controller 56 then may provide an estimate of interfacial tension, using the pendent drop method, well known to persons skilled in the art, to determine the interfacial tension of the mixture at thermodynamic equilibrium. Measurements may be repeated for several drops suspended from end 54 in order to obtain more reliable data. Controller 56 also controls motor 37 to move piston 33 upwardly, in the direction of arrow 134, or downwardly, in the direction of arrow 136, to maintain a constant pressure in upper portion 18, as measured by pressure transducers 84 and 90.

ISOTHERMAL OR CONSTANT COMPOSITION EXPANSION

Figure 7:
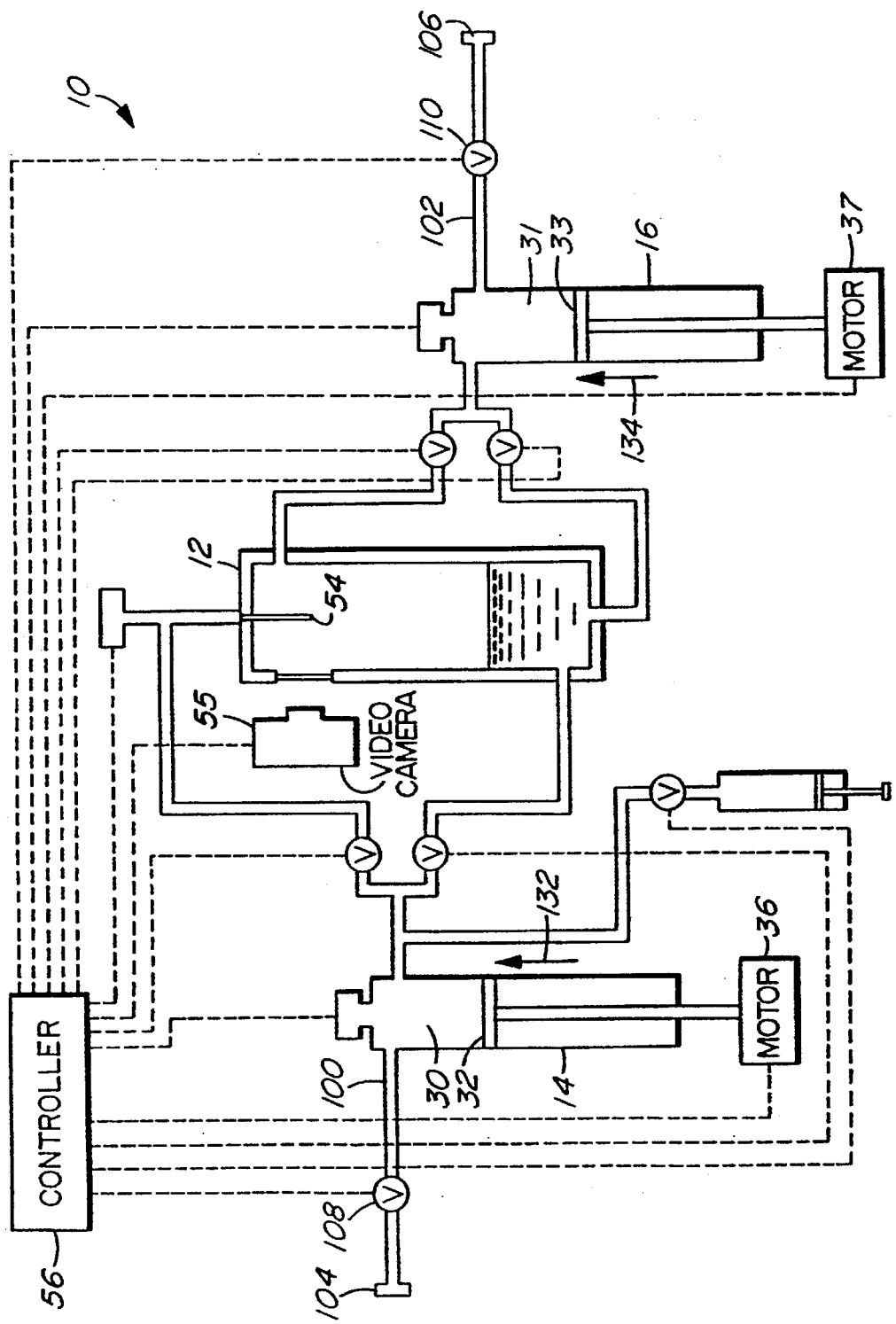
FIG. 7 is a schematic view of the apparatus of FIG. 1 depicting use of the apparatus for the measurement of isothermal or constant composition expansion.

The use of apparatus 10 for the measurement of isothermal or constant composition expansion will now be discussed with reference to FIG. 7. Isothermal or constant composition expansion experiments are routine tests undertaken on reservoir samples by manipulating pressure, volume or temperature of the sample to obtain relevant data.

The pressure in apparatus 10 is adjusted through reduction of the volume in variable volume chambers 14 and 16 by moving pistons 32 and 33 upwardly in the direction of arrows 132 and 134, respectively. The pressure is increased until the sample is above its saturation pressure and the mixture returns to a homogeneous single phase with the less dense phase dissolved in the more dense phase of the mixture. Controller 56 then controls the volume in chambers 30 and 31 above respective pistons 32 and 33 so that the total volume in variable volume chambers 30 and 31 above respective pistons 32 and 33, together with the volume of chamber 12, increases over time in a step-by-step manner. This causes a corresponding pressure decline until a predetermined lower pressure amount is attained. At each pressure level "i", isothermal compressibility is estimated according to the formula:

$$C_{it}=(V_{i+1}-V_i)/(P_{i+1}-P_i)/V_i$$

where $C_{it}$ is isothermal compressibility;

$V_i$ is the total volume in variable volume chambers 30 and 31 above respective pistons 32 and 33, together with the volume of chamber 12;

i is an integer defining each step; and $P_i$ is the pressure in the variable volume chambers 30 and 31 above respective pistons 32 and 33, and in chamber 12.

A phase transition is noted by controller 56 by a numerical discontinuity in the compressibility estimate $C_{it}$ or by camera 55 in electronically capturing minute bubbles or droplets exhausting through end 54.

While compressibility estimates may be determined with no regard for relative phase volume, saturations require that care be taken to permit gravity segregation to separate the phases or components, ensuring that correct phase volumes are measured in the cell. This may be done by using a time sequence of video images to estimate when a constant phase level occurs. The saturation of a component at step (i) is:

$$S_{ip}=V_{ip}/V_i$$

where $S_{ip}$ is the saturation of phase p at the step i; and $V_{ip}$ is the volume of the phase p at the step i.

DIFFERENTIAL LIBERATION

Figure 8:
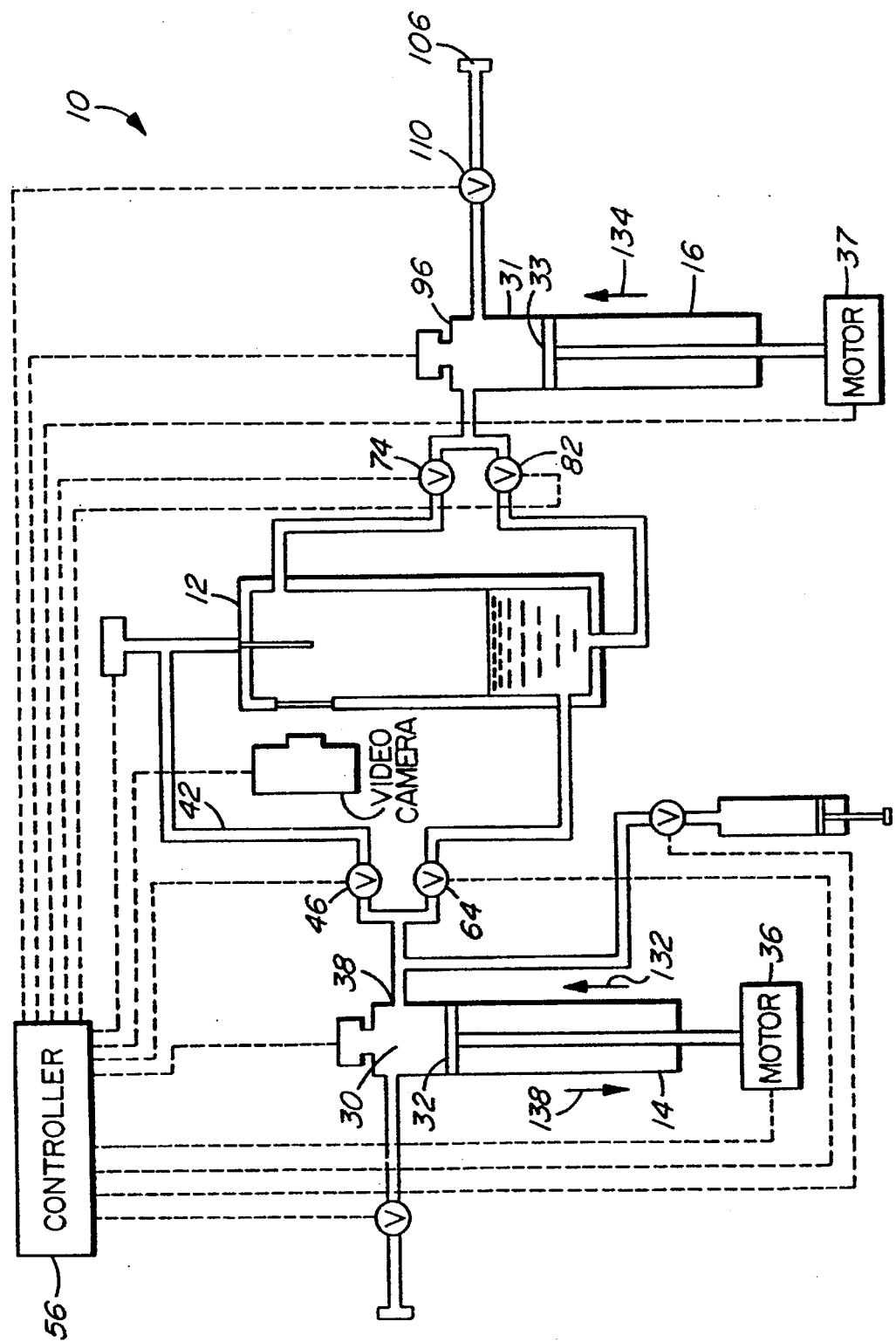
FIG. 8 is a schematic view of the apparatus of FIG. 1 showing the use of the apparatus for determining differential liberation of the mixture.

The use of apparatus 10 for determining differential liberation of the mixture will now be discussed with reference to FIG. 8. Controller 56 activates motors 36 and 37 to move respective pistons 32 and 33 to increase the pressure of the sample in the system above the saturation pressure to provide a homogeneous single phase mixture of sample. Preferably, the volume above pistons 32 and 33 in respect of chambers 30 and 31 is about 35 milliliters each. Controller 56 controls motors 36 and 37 and valves 46, 64, 74, and 82 so that the total volume in chambers 14 and 16 above pistons 32 and 33, plus the volume of fixed volume chamber 12 (Vt), is increased, with a corresponding pressure decline, until a lower pressure limit or volume expansion is reached. Equilibrium is attained by use of apparatus 10 in the manner described above under "OPERATION". Controller 56 can control the valves and movement of respective pistons 32 and 33, in a manner so that pump A contains all more dense component with none of the less dense component in chamber 30. This is done by repeatedly expanding chamber 30 with valve 64 open, and valve 46 closed and repeatedly contacting chamber 30 with valve 64 closed and value 46 open. Measurement of the total volume of the less dense phase may be determined through the position of piston 33 as indicated by motor 37 to controller 56, and by the interface position in chamber 12. With valves 74 and 82 in their closed position and valve 110 in its open position, all of the less dense component may be exhausted from chamber 31 by movement of piston 33 upwardly, in the direction of arrow 134, to the piston 33 uppermost position adjacent upper end face 96. A sample container may be attached to input port 106 for sealing engagement to prevent loss of less dense component, or introduction of air into apparatus 10. Less dense component is captured in the sample bottle and adjustments are made to adjust the pressure and temperature and volume at standard conditions is measured as $V_{igsc}$.

The present invention is primarily discussed with reference to application in the oil and gas industry for obtaining maximum extraction of oil and gas mixtures from underground reservoir sites. However, it should be understood that this invention is of more general application and is adaptable to other fields of use where mixtures of components of differing densities must be analyzed to facilitate the extraction of relevant components from a source material. This includes:

(a) high pressure, dense gas extraction of essential oils, oleoresin, and other flavour, fragrance and pharmaceutical components from herbaceous raw materials; and (b) refining processes for separation and fractionation of petroleum oils, essential oils and oleoresin.

We claim:

1. An apparatus for setting a desired P-V-T thermodynamic state and for facilitating thermodynamic equilibrium of mixtures of liquids, vapours or a combination thereof, said mixtures comprising differing molecular components, the apparatus comprising:

(a) a fixed volume chamber having an upper portion and a lower portion defined by transversely disposed upper and lower end faces connected by a wall;

(b) a first variable volume chamber for containing primarily more dense components or phases of the mixture;

(c) a second variable volume chamber for containing primarily less dense components or phases of the mixture;

(d) an upper end conduit having a first end extending through the upper end face adjacent the upper portion into the fixed volume chamber and a second end connected to the first variable volume chamber;

(e) a lower end conduit having a first end extending through the lower end face adjacent the lower portion into the fixed volume chamber and a second end connected to the second variable volume chamber;

(f) an upper wall conduit having a first end extending through the wall adjacent the upper portion into the fixed volume chamber and a second end connected to the second variable volume chamber;

(g) a lower wall conduit having a first end extending through the wall adjacent the lower portion into the fixed volume chamber and a second end connected to the first variable volume chamber;

(h) an upper end conduit valve connected to the upper end conduit for controlling the flow of the mixture through the upper end conduit;

(i) a lower end conduit valve connected to the lower end conduit for controlling the flow of the mixture through the lower end conduit;

(j) an upper wall conduit valve connected to the upper wall conduit for controlling the flow of the mixture through the upper wall conduit;

(k) a lower wall conduit valve connected to the lower wall conduit for controlling the flow of the mixture through the lower wall conduit;

(l) a valve controller for selectively controlling the positions of the upper end conduit, lower end conduit, upper wall conduit and lower wall conduit valves to orient the valves in open or closed positions to direct the flow of mixture between the first and second variable volume chambers and the fixed volume chamber to selectively cause more dense component of the mixture to flow through less dense component of the mixture and less dense component of the mixture to flow through more dense component of the mixture, the flow through occurring within the fixed volume chamber.

2. The apparatus described in claim 1, wherein the valve controller controls the valves to alternate between a first position in which:

(a) the upper end conduit and upper wall conduit valves are open to permit flow through the upper end conduit and upper wall conduit on change in volume of the first and second variable volume chambers; and (b) the lower end conduit and lower wall conduit valves are closed to prevent flow through the lower end conduit and lower wall conduit;

whereby the more dense component in the first variable volume chamber may flow through the less dense component in the upper portion of the fixed volume chamber and the less dense component may exit the fixed volume chamber into the second variable volume chamber when the volume in the first chamber is decreased and the volume in the second chamber is increased;

and a second position in which:

(a) the lower wall conduit and upper wall conduit valves are open to permit flow through the lower wall conduit and upper wall conduit on a change in volume of the first and second variable volume chambers, and;

(b) the upper end conduit and lower end conduit valves are closed to prevent flow through the upper and lower end conduits;

whereby the less dense component in the second variable volume chamber may enter the less dense component in the upper portion of the fixed volume chamber and more dense component may exit the fixed volume chamber into the first variable volume chamber when the volume in the second chamber is decreased and the volume in the first chamber is increased.

3. The apparatus described in claim 2, further comprising a pressure regulator communicating with the second variable volume chamber for determining the pressure within the first and second variable volume chambers and the fixed volume chamber, the pressure regulator controlling the volume in the second variable volume chamber to maintain a substantially constant predetermined pressure in the first and second variable volume chambers and the fixed volume chamber.

4. The apparatus described in claim 1, wherein the controller controls the valves between a first position in which:

(a) the lower end conduit and lower wall conduit valves are open to permit flow through the lower end conduit and lower wall conduit on change in volume of the first and second variable volume chambers; and (b) the upper end conduit and upper wall conduit valves are closed to prevent flow through the upper end conduit and upper wall conduit;

whereby the less dense component in the second variable volume chamber may flow through the more dense component in the lower portion of the fixed volume chamber and more dense component may exit the fixed volume chamber into the first variable volume chamber when the volume in the second chamber is decreased and the volume in the first chamber is increased;

and a second position in which:

(a) the upper end conduit and upper wall conduit valves are open to permit flow through the upper end conduit and upper wall conduit on change in volume of the first and second variable volume chambers; and (b) the lower end conduit and lower wall conduit valves are closed to prevent flow through the lower end conduit and lower wall conduit;

whereby the more dense component in the first variable volume chamber may flow through the less dense component in the upper portion of the fixed volume chamber and less dense component may exit the fixed volume chamber into the second variable volume chamber when the volume in the first chamber is decreased and the volume in the second chamber is increased.

5. The apparatus described in claim 4, further comprising first volume regulator communicating with the first variable volume chamber for determining the volume in the first variable volume chamber and second volume regulator communicating with the second variable volume chamber for determining the volume in the second variable volume chamber, said first and second volume regulators controlling the respective volumes in the first and second variable volume chambers to maintain a constant total volume of both the first and second variable volume chambers.

6. The apparatus described in claim 1, wherein the valve controller controls the valves to alternate between a first position in which:

(a) the more dense component is directed into the chamber from the first variable volume chamber into the fixed volume chamber by means of the upper end conduit; and (b) the less dense component is directed out of the fixed volume chamber into the second variable volume chamber by means of the lower end conduit;

and a second position in which:

(a) the less dense component is directed from the second variable volume chamber to the fixed volume chamber by means of the lower end conduit; and (b) the more dense component is directed out of the fixed volume chamber into the first variable volume chamber by means of the lower side conduit.

7. The apparatus described in claim 6, further comprising a pressure regulator communicating with the second variable volume chamber for determining the pressure in the second variable volume chamber, wherein the volume in the first and second variable volume chambers is controlled by the pressure regulator to maintain the pressure in the fixed volume chamber substantially at a predetermined pressure.

8. The apparatus described in claim 6, further comprising first volume regulator for determining and controlling the volume of the first variable volume chamber and second volume regulator for determining and controlling the volume in the second variable volume chamber, the first and second volume regulators controlling the respective volume in the first and second variable volume chambers to maintain a constant total volume of both the first and second variable volume chambers.

9. An apparatus as described in claim 1, further comprising:

(a) pressure regulator communicating with the fixed volume chamber for determining the pressure within the fixed volume chamber and for controlling the volumes in the first and second variable volume chambers;

(b) first volume regulator communicating with the first variable volume chamber for determining the volume in the first variable volume chamber and second volume regulator communicating with second variable volume chamber for determining the volume in the second variable volume chamber, and;

(c) system controller connected to the first and second volume regulators and the pressure regulator to control the volumes in the first and second variable volume chambers to maintain either constant total volume of the first and second variable volume chambers or to maintain constant pressure in the fixed volume chamber, the system controller receiving pressure data from the said pressure regulator for controlling constant pressure in the fixed volume chamber and volume data from the first and second volume regulators for controlling constant total volume in the first and second variable volume chambers.

10. The apparatus described in claim 9, wherein the system controller controls the valve controller to switch repeatedly between the first and second valve positions until the mixtures is substantially at thermodynamic equilibrium.

11. The apparatus described in claim 10, wherein the system controller determines when thermodynamic equilibrium of the mixture has been substantially attained, based on a reduction in the change in total volume in the first and second variable volume chambers decreases below a predetermined level.

12. The apparatus described in claim 1, wherein the fixed volume chamber further comprises a clear portion for viewing the interior of the fixed volume chamber.

13. The apparatus as described in claim 12, further comprising an upper end port capillary tube connecting the first end of the upper end conduit to the interior of the fixed volume chamber, the capillary tube dimensioned to permit drop-by-drop flow of mixture into the fixed volume chamber.

14. The apparatus described in claim 13, wherein the clear portion permits viewing of the drop-by-drop flow of mixture from the capillary tube into the fixed volume chamber.

15. The apparatus described in claim 13, further comprising a third variable volume chamber comprising a hand actuated controller to vary the volume in the third variable volume chamber, said third variable volume chamber connected to the upper end conduit to permit manual control of the pressure in the upper end conduit to control the drop-by-drop flow rate of the mixture through the capillary tube.

16. The apparatus as described in claim 13, further comprising video frame capturing camera for determining predetermined characteristics of the drops of the drop-by-drop mixture flow from the capillary, the camera aimed at the clear portion and communicating with the system controller to provide an estimate of interfacial tension between more dense and less dense components of the mixture, based on the pendent drop method of calculation.

17. The apparatus described in claim 16, wherein the interfacial tension results obtained by the system controller are used as preliminary data in a computer model of a reservoir to enable the computer model to generate maintenance parameters for an actual reservoir site.

18. A method for attaining substantial thermodynamic equilibrium of mixtures of liquids, vapours or a combination thereof, the mixtures comprising components of different densities, in an apparatus having a fixed volume chamber connected to a first variable volume chamber containing primarily the more dense component and a second variable volume container containing primarily the less dense component, comprising the steps of:

(a) simultaneously:

(i) introducing a flow of the more dense component from the first variable volume chamber into an upper region of the fixed volume chamber; and (ii) exhausting less dense component into the second variable volume chamber from the upper region of the fixed volume chamber;

whereby the more dense component flows through the less dense component in the upper region of the fixed volume chamber;

(b) simultaneously:
  (i) introducing a flow of less dense component from the second variable volume container into a lower region of the fixed volume chamber; and
  (ii) exhausting more dense component from the lower region of the fixed volume chamber;
whereby the less dense component flows through the more dense component in the lower region of the fixed volume chamber; and (c) monitoring the pressure in the fixed volume chamber;

(d) regulating the volume in the first and second variable volume chambers during steps (a), (b) and (c) to maintain a constant predetermined pressure in the fixed volume chamber and monitoring the pressure in the fixed volume chamber; and (e) repeating steps (a), (b), (c) and (d) until the change in volume of the first and second variable volume chambers required to maintain the constant pre-determined pressure is below a pre-determined volume amount indicative of substantial thermodynamic equilibrium of the mixture in the fixed volume chamber.

19. The method as described in claim 18 further comprising the steps of:

(f) simultaneously:
  (i) introducing a flow of the less dense component into the lower region of the fixed volume chamber; and
  (ii) exhausting more dense component from the lower region of the fixed volume chamber;
whereby the less dense component flows through the more dense component in the lower region of the fixed volume chamber; and (g) simultaneously:
  (i) introducing a flow of the more dense component into an upper region of the fixed volume chamber; and
  (ii) exhausting less dense component from a lower region of the fixed volume chamber;
whereby the more dense component flows through the less dense component in the upper region of the fixed volume chamber; and (h) regulating the total volume in the first and second variable volume chambers during steps (f) and (g), to maintain the total volume in the first and second variable volume chambers substantially constant; and (i) repeating steps (f), (g) and (h) until the change in pressure in the fixed volume chamber is below a pre-determined amount indicative of substantial thermodynamic equilibrium of the mixture in the fixed volume chamber.

* * * * *